Feb. 23, 1965 H. KERRIGAN Plant Pat. 2,485
AZALEA PLANT
Filed Dec. 26, 1963
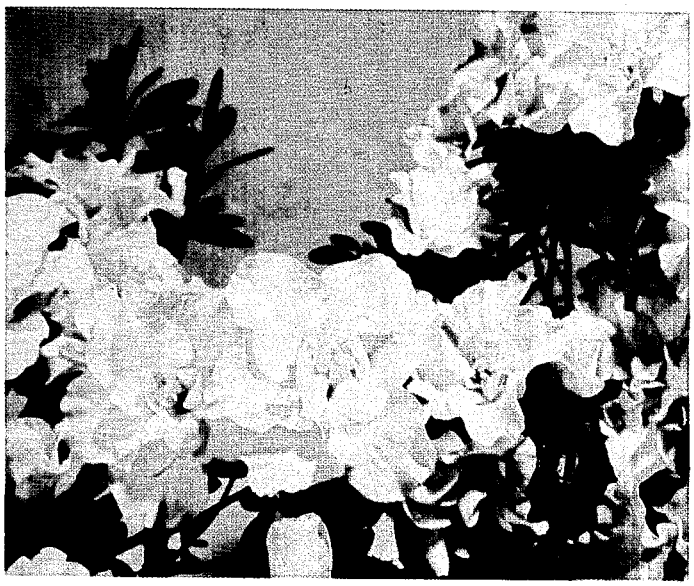
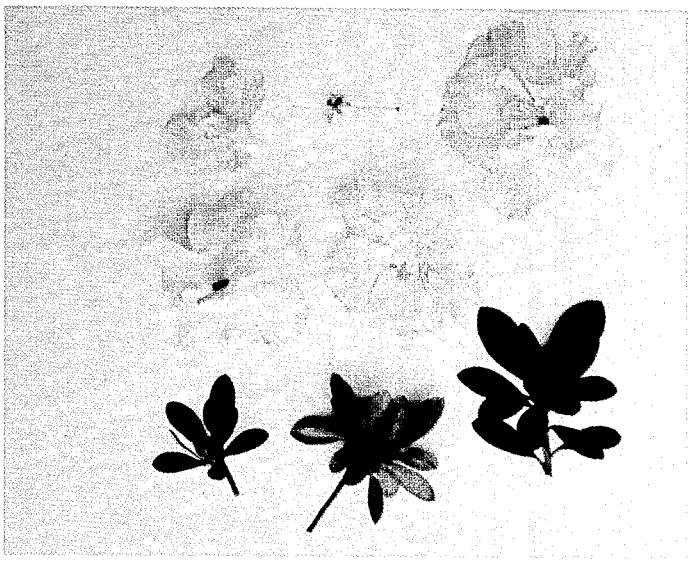

United States Patent Office

Plant Pat. 2,485
Patented Feb. 23, 1965

2,485
AZALEA PLANT

Howard Kerrigan, 3003 Totterdell St., Oakland, Calif.

Filed Dec. 26, 1963, Ser. No. 333,777
1 Claim. (Cl. Plt.—56)

This disclosure concerns a new and distinct variety of azalea of the florist's forcing type, particularly that group of azaleas known in the trade as the Belgian Indicas. My new variey is a sport (somatic mutation) of the variety Happy Holiday, which was a sport of the well-known variety Paul Schäme. Happy Holiday differed from Paul Schäme only in the color of the flowers which are essentially white, salt and peppered pink. My new variety differs from Paul Schäme and Happy Holiday in having a uniformly colored flower of Dawn Pink to Porcelain Rose. It also differs from the well-known sport of Paul Schäme, Erie (syn. Eric Schäme) in that there is no white border to the flower. The colors of Paul Schäme and Erie are also much more coral toned than is my variety.

This sport was discovered by me in a commercial population of plants of Happy Holiday being grown by me at Oakland, California, in 1955. It has proven completely stable through a series of sequential generations of asexually reproduced plants grown by me at Oakland, California, from soft wood cuttings since 1955.

The characteristics of my new variety are disclosed in the following descriptions and in the accompanying drawing which depicts my new variety substantially as it appears in nature and as accurately as presently available methods will permit. The color designations employed are those given in the Horticultural Colour Chart (HCC) published by Wilson Colour Ltd., in collaboration with the Royal Horticultural Society.

*Horticultural description*

Plant growth and habit essentially identical to that of the varieties Paul Schäme, Erie and Happy Holiday. The distinguishing difference lies in the color of the flower which is Dawn Pink (HCC 523/1) to Porcelain Rose (HCC 620/2). The variation in color depends upon the conditions prevailing at the time the plant is being brought into bloom. Warm ambient temperatures encourage the lighter tones while cooler ones tend to produce somewhat more highly saturated colors. Also during cool climatic episodes a more or less conspicuous salt and pepper pattern may develop which is characterized by small areas of more intense pigmentation scattered over the ground color of the corolla. There is no variation in color between plants brought into flower at the same time.

To my knowledge this color does not now exist in a plant with the recognized overall superiority of Paul Schäme and my new variety constitutes an especially vlauable addition to the list of florist's forcing azaleas.

*Botanical description*

Plant upright, full, heavily branched. Stems green, appearing rufescent because of the heavy chestnut strigae. Foliage medium green 1½ to 2 inches long and 7/16 to ¾ inch wide; petiolate. The petioles short, ⅛ to 3/16 inch long. The leaf margin is entire, ciliate, the cilia somewhat patent. The leaf apex is bluntly mucronate. The lamina is oblate, shiny above, somewhat pubescent, the hairs are tan, evenly scattered, adpressed, and conspicuous. The lower surface of the leaf is much lighter than the upper, glaucous, moderately pubescent, the hairs scattered in intervenal areas. Mid-vein of the lamina prominent, conspicuous, appearing tan because of the dense, adpressed pubescence. Secondary veins barely prominent. The buds of the inflorescence are covered with a dense, silky pubescence obscuring the individual scales. The pubescence is rich tan to straw colored.

The flowers are borne in umbelate clusters of 2–3 on stout pedicels ½ inch long and 3/32 inch in diameter. The pedicels are moderately pubescent. The hairs are long, silky, light tan to white.

The calyx is normal, green, five lobed. The sepals are ⅜ inch long and 5/32 inch wide at their bases, tri-angular. Their margins are entire, and the apices are pointed. The reverse of the sepals is densely pubescent while the obverse is glabrous to slightly pubescent. The bases of the sepals are marked white. The corolla is pink, petamerous, very broadly flaring, 1¼ inches deep by 3¾ inches across. The tube is short, widely flaring, ⅝ inch deep by 1¼ inches across. The limbs are broadly circular, auriculate with undulate margins. The stamens are modified into large staminodia. The outer whorl is ordnarily adnate to the corolla. The three or four outermost staminodia are smaller, the lobes ¾ inch long by 9/16 inch wide. The second whorl of staminodia are large, showy, deeply cut, frilled and ruffled, variously fused at their bases forming an imperfect tube. The limbs of this whorl are 1½ inches long by 1¾ inches wide. Adnate to these large showy staminodia is a third series of smaller ones, 4–5 in number which appear as appendages to the large second series and which gives the flower the appearance of being heavily ruffled. Another tissue often develops on these innermost staminodia. At the base of the ovary there are five small, yet conspicuous, triangular scales. The pistil is 15/16 inches long. The stigma is large, 3/32 inch across, ivory with small pink maculae, inconspicuously 5–7 lobed oriented normal to the floral axis. The style is 11/16 inch long slightly tapering 1/16 inch in diameter proximally 1/32 inch in diameter at the narrowest point gently flaring along the distal third of its length to 3/64 inch diameter at the base of the stigma, slightly curved or straight, never stigmoid, greenish proximally, pinkish distally.

The ovary is small, ⅛ inch long, dark green, conical, densely silky-pubescent, the hairs long exceeding the ovary by over ½ its length and obscuring it.

Having disclosed my invention in the above descriptions and in the accompanying drawings what I claim as new and patentable is:

A new and distinct variety of azalea of the Belgian Indica type essentially identical with the variety Paul Schäme except for the flower color which is a uniform Dawn Pink to Porcelain Rose producing an overall color tonality that is unique in azaleas of this type.

No references cited.

ABRAHAM G. STONE, *Primary Examiner.*